(12) United States Patent
Hedberg et al.

(10) Patent No.: US 8,918,165 B2
(45) Date of Patent: Dec. 23, 2014

(54) MEDICAL DEVICE FOR POSITIONING OF A LEAD

(71) Applicant: St. Jude Medical AB, Jarfalla (SE)

(72) Inventors: Sven-Erik Hedberg, Kungsangen (SE); Nils Holmstrom, Jarfalla (SE); Johan Eckerdal, Knivsta (SE); Torbjorn Persson, Malmo (SE); Rolf Hill, Jarfalla (SE); Fredrik Westman, Akersberga (SE)

(73) Assignee: St. Jude Medical AB, Jarfalla (SE)

( * ) Notice: Subject to any disclaimer, the term of this patent is extended or adjusted under 35 U.S.C. 154(b) by 130 days.

(21) Appl. No.: 13/631,570

(22) Filed: Sep. 28, 2012

(65) Prior Publication Data

US 2014/0094706 A1 Apr. 3, 2014

(51) Int. Cl.
*A61B 5/042* (2006.01)

(52) U.S. Cl.
USPC .............................. 600/509; 607/28

(58) Field of Classification Search
USPC .................. 600/373–377, 508–513, 547; 607/119–126, 27, 28
See application file for complete search history.

(56) References Cited

U.S. PATENT DOCUMENTS

| 7,450,999 | B1 | 11/2008 | Karicherla et al. | |
| 7,824,341 | B2 * | 11/2010 | Krishnan | 600/508 |
| 7,974,675 | B2 | 7/2011 | Doan | |
| 2008/0255470 | A1 * | 10/2008 | Hauck et al. | 600/547 |
| 2009/0163822 | A1 | 6/2009 | Doan | |
| 2010/0298841 | A1 * | 11/2010 | Prinzen et al. | 606/129 |

* cited by examiner

*Primary Examiner* — Scott Getzow (57) ABSTRACT

The present invention relates generally to medical devices for electrode positioning during implantation procedures. A cardiac signal measuring device measures cardiac signals sensitive to inherent differences between cardiac tissue and blood using at least one electrode of a medical lead arranged at a distal tip of the medical lead and at least a second electrode arranged at a distance from the distal electrode and being connectable to the measuring unit. An analyzing module acquires cardiac signals measured during predetermined measurement sessions. The analyzing module determines at least one cardiac signal value based on the cardiac signals for each measurement session and analyzes changes of the cardiac signal values between different measurement sessions to determine a position of the electrode relative a tissue border. A maximum of the change of the cardiac signal values between two successive measurement sessions indicates that the electrode has reached the tissue border.

7 Claims, 7 Drawing Sheets

MEDICAL DEVICE FOR POSITIONING OF A LEAD

FIELD OF THE INVENTION

The present invention relates generally to medical devices for electrode positioning, for example, during implantation procedures.

BACKGROUND OF THE INVENTION

When delivering pacing stimulation to the left ventricle of the patient's heart, it is beneficial to provide the pacing in the endocardium so as to achieve synchronized heart beats as the activation time of the left ventricle is reduced compared to epicardial pacing. In both cases, it is the myocardial cells adjacent to the endo- and epicardium, respectively, which are stimulated, not the endocardium or epicardium.

The subendocardial muscle is a thin layer, about half a millimeter thick. A stimulation electrode should be placed close to this layer in order to take advantage of the positive effects of pacing the myocardial cells close to the endocardium. Placement of an endocardial lead via the left ventricle is characterized by an increased risk of thromboembolic events. Endocardial pacing of the left ventricle can be achieved by a transseptal pacing lead via intraventricular septum, eliminating the risk for thromboembolic events by lead exposure in the blood flow of the left ventricle.

However, placement of an intramural pacing electrode via septum for the purpose of endocardial stimulation should therefore be close to the endocardium to ensure similar performance to an activation fixation lead implanted from the endocardial side. When placing the pacing electrode via septum, it is thus very important that the position of the electrode relative to the septum can be determined with a high degree of accuracy.

SUMMARY OF THE INVENTION

An object of the present invention is to provide a medical device and a method for determining the position of a pacing electrode relative to cardiac tissue with a high degree of accuracy.

A further object of the present invention is to provide a medical device and a method for determining the position of a pacing electrode relative to cardiac tissue with a high degree of accuracy during an implantation procedure.

These and other objects of the present invention are achieved by means of an implantable medical device and a method having the features defined in the independent claims. Embodiments of the invention are characterized by the dependent claims.

According to an aspect of the present invention there is provided a medical device for determining a desired position at a tissue border of a medical lead having a distal tip being arranged to enable penetration of cardiac tissue, the lead being connectable to a measuring unit of the medical device at a proximal end. The measuring unit comprises a cardiac signal measuring device configured to measure cardiac signals sensitive to inherent differences between cardiac tissue and blood using at least one electrode of the medical lead arranged in close proximity to a distal tip of the medical lead and at least a second electrode arranged at a distance from the distal electrode and being connectable to the measuring unit. Further, an analyzing module communicating with the cardiac signal measuring device is configured to acquire cardiac signals from the cardiac signal measuring device measured during predetermined measurement sessions. The analyzing module is further configured to determine at least one cardiac signal value based on the cardiac signals for each measurement session and to analyze changes of the cardiac signal values between different measurement sessions to determine a position of the distal tip electrode relative a tissue border, wherein a maximum of the change of the cardiac signal values between two successive measurement sessions indicates that the distal tip electrode has reached the desired position at the tissue border.

According to another aspect of the present invention, there is provided a method for method for determining a desired position at a tissue border of a medical lead having a distal tip being arranged to enable penetration of cardiac tissue. The method comprises measuring cardiac signals sensitive to inherent differences between cardiac tissue and blood using at least one electrode arranged at the distal tip of the medical lead and at least a second electrode arranged at a distance from the distal tip electrode, acquiring cardiac signals measured at predetermined measurement sessions. Further, at least one cardiac signal value is determined based on the cardiac signals for each measurement session and changes of the cardiac signal values between different measurement sessions is analyzed to determine a position of the distal tip electrode relative a tissue border, wherein a maximum of the change of the cardiac signal values between two successive measurement sessions indicates that the distal tip electrode has reached the desired position at the tissue border.

The present invention is based on the insight that cardiac signals sensitive to inherent differences in tissue structure between blood and cardiac tissue can be used to precisely indicate when an electrode has crossed a tissue border between cardiac tissue and blood. For example, the different conductivities of blood and cardiac tissue can be used to provide a precise indication of whether an electrode has crossed a border between cardiac tissue and blood. Further, changes in IECG amplitude due to a distance to activated cardiac cells can be used to provide a precise indication of whether an electrode has crossed a border between cardiac tissue and blood. This precise indication can, in turn, be used to place the electrode in a position very close to a tissue wall or tissue border during an implantation procedure.

According to the present invention, cardiac signals sensitive to these differences, e.g. different conductivities, are repeatedly measured at predetermined measurement sessions. Preferably, the distal tip electrode is gradually advanced step-by-step in small increments through the tissue towards the tissue border and the measurement sessions are performed when the movement of the distal tip electrode is stopped at two successive positions. The cardiac signals obtained at the different measurement sessions are analyzed to identify changes in the signals between successive positions reflecting the position of the distal tip electrode relative the tissue border. The inventors have found that, for example, a value or feature of the cardiac signals such as impedance and/or IECG signals obtained at two positions is stable, i.e. does not change to any substantial extent, when the distal tip electrode is moved between different positions within the tissue relative the tissue border but decreases very rapidly over a short distance when the distal tip electrode reaches positions in close proximity to the tissue border. Such values or features include, but are not limited to, the maximum amplitude over a cardiac cycle, the average maximum amplitude over a number of cardiac cycles, the peak-to-peak value over a cardiac cycle, the average peak-to-peak value over a number of cardiac cycles, the waveform morphology over a cardiac cycle, or the average morphology over a number of cardiac cycles.

In particular, the inventors have found that when the distal tip electrode is moved between successive positions very close to the tissue border, the derivative of the cardiac signal with respect to the distance between the positions reaches a maximum. This phenomenon also occurs if the distal tip electrode is moved through blood towards a tissue border. That is, the observed value or feature, e.g. the maximum amplitude or peak-to-peak value, is stable, or more or less constant, when the distal tip electrode is moved between different positions in the blood at a distance from the tissue border. However, in this latter case, the observed value or feature, e.g. the maximum amplitude or peak-to-peak value, will instead increase very rapidly when the distal tip electrode reaches positions at the tissue border and eventually penetrates the tissue border.

According to embodiments of the present invention, the cardiac signal measuring device comprises an impedance measuring module configured to measure impedance signals. The analyzing module is configured to acquire impedance signals from the impedance signal measuring module measured at predetermined measurement sessions. Further, the analyzing module is configured to determine at least one impedance signal value based on the impedance signals for each measurement session, and to analyze changes of the impedance signal values between different measurement sessions to determine a position of the distal tip electrode relative a tissue border, wherein a maximum of the change of the impedance signal values between two successive measurement sessions indicates that the electrode has reached the desired position at the tissue border.

According to embodiments of the present invention, the cardiac signal measuring device comprises an intracardiac electrogram, IECG, measuring module configured to measure IECG signals. The analyzing module is configured to acquire IECG signals from the IECG measuring module measured at predetermined measurement sessions. Moreover, the analyzing module is configured to determine at least one IECG signal value based on the IECG signals for each measurement session, and to analyze changes of the IECG signal values between different measurement sessions to determine a position of the distal tip electrode relative a tissue border, wherein a maximum of the change of the IECG signal values between two successive measurement sessions indicates that the distal tip electrode has reached the desired position at the tissue border According to embodiments of the present invention, the cardiac signal measuring device comprises an intracardiac electrogram, IECG, measuring module configured to measure IECG signals and an impedance measuring module configured to measure impedance signals. The analyzing module is configured to acquire IECG signals from the IECG measuring module and impedance signals from the impedance measuring module measured at measurement sessions. The analyzing module is configured to determine at least one IECG signal value based on the IECG signals and at least one impedance signal value based on the impedance signals for each measurement session. Further, the analyzing module is configured to analyze changes of the IECG signal values and impedance signal values between different measurement sessions to determine a position of the distal tip electrode of the lead relative a tissue border, wherein a maximum of the change of the IECG signal values and the impedance signal values between two successive measurement sessions indicates that the electrode has reached the desired position at the tissue border.

According to embodiments of the present invention, the measuring unit is configured to synchronize impedance signal measurements and IECG signal measurements in time during the measurement sessions. The analyzing module is configured to acquire impedance signals and IECG signals from the impedance signal measuring module and IECG measuring module measured at synchronized and predetermined measurements sessions, determine the synchronized impedance signal values and/or IECG signal values for each measurement session, and analyze synchronous changes of the impedance signal values and the IECG signal values to determine a position of the distal tip electrode of the lead relative to a tissue border, wherein a synchronous maximum of a change of the impedance signal values and the IECG signal values between two successive measurement sessions or positions indicate that the distal tip electrode has reached the desired position at the tissue border.

According to embodiments of the present invention, QRS-waveforms are determined for each cardiac cycle using IECG signals and the impedance signal values are synchronized with the QRS-waveforms. Changes between different measurements of the impedance signal values coinciding with a certain point of the QRS-waveform, for example the peak of the R wave, are analyzed to determine a position of the distal tip electrode relative a tissue border, wherein a maximum of the change of the impedance signal values between two successive measurement sessions or positions indicate that the distal tip electrode has reached the desired position at the tissue border. Hence, impedance signal values that coincide in time in respective cardiac cycle are compared and thereby disturbances in the impedance signals caused by contractions and extractions of the heart can be significantly reduced.

According to embodiments of the present invention, an intramural pacing electrode can be placed very close to endocardium via septum and thereby a similar performance to a fixation lead implanted from the endocardial side can be ensured without the negative effects such as risk for thromboembolic events resulting from such a placement.

According to embodiments of the present invention, the at least one second electrode is a ring electrode arranged on a guiding catheter, the guiding catheter being arranged to guide the lead during penetration of tissue.

According to other embodiments of the present invention, the at least one second electrode is arranged to be in a position outside the heart and being arranged to be connected to the measuring unit. For example, the fixed electrode may be an indifferent temporary electrode placed at a fixed position relative the heart outside the heart.

Further objects and advantages of the present invention will be discussed below by means of exemplifying embodiments.

These and other features, aspects and advantages of the invention will be more fully understood when considered with respect to the following detailed description, appended claims and accompanying drawings.

BRIEF DESCRIPTION OF THE DRAWINGS

Exemplifying embodiments of the invention are illustrated by way of example and not by way of limitation in the figures of the accompanying drawings in which like references indicate similar elements. It should be noted that references to "an" or "one" embodiment in this description are not necessarily to the same embodiment, and such references mean at least one.

DESCRIPTION OF EXEMPLIFYING EMBODIMENTS

The following is a description of exemplifying embodiments in accordance with the present invention. This description is not to be taken in limiting sense, but is made merely for the purposes of describing the general principles of the invention. It is to be understood that other embodiments may be utilized and structural and logical changes may be made without departing from the scope of the present invention.

In the following, the present invention will be described in the context of positioning of a transseptal lead at the endocardial border via septum to obtain similar performance to an active fixation lead implanted from the endocardial side but without the negative effects associated with this placement such as increased risk for thromboembolic events. However, the present invention is not limited to transseptal leads but may be utilized for positioning other types of leads, for example, for positioning a lead penetrating the atrial septum for placement at the atrial septum border between septum and left atrium.

Figure 10:
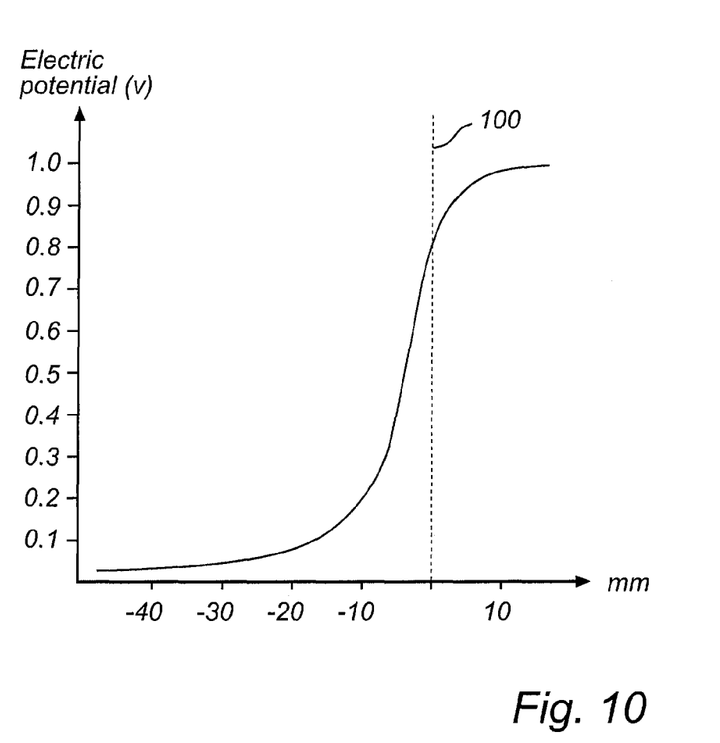
FIG. 10 is a diagram illustrating the electric potential as a function of the position of an electrode relative to a tissue border.

The present invention is based on the insight that cardiac signals sensitive to inherent differences, e.g. conductivity differences between blood and tissue can be used to accurately determine a position of an electrode relative to a cardiac tissue border. In FIG. 10, simulations of the electric potential as a function of different positions of an electrode in blood/tissue environment are illustrated. As can be seen, the electric potential is relatively constant in tissue and in blood when measured at a distance from a tissue border. However, when the electrode reaches a position at a close proximity to the tissue border (indicated with the dashed line 100) from the tissue side, the electric potential decreases very rapidly over a short distance. The electric potential starts to decrease when the electrode is close to the tissue border 100, about 2-4 mm from the tissue border 100, and then falls rapidly when the tissue border is reached and penetrated. Inversely, if the electrode approaches the tissue border from the blood side, the electric potential starts to increase when the electrode is close to the tissue border 100, about 10 mm from the tissue border 100, and increases rapidly when the tissue border 100 is reached and penetrated.

Figure 1:
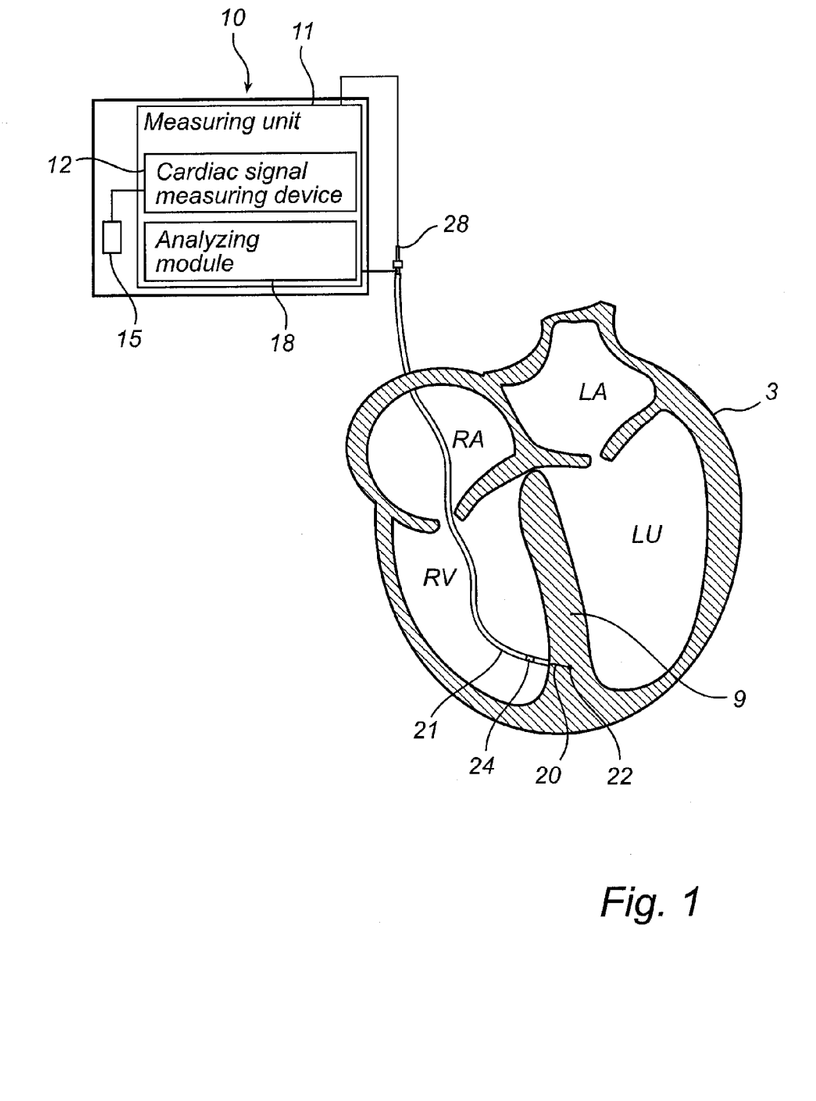
FIG. 1 is a simplified and schematic illustration of one embodiment of a medical device connected to a transseptal lead positioned within a heart.

Turning now to FIG. 1, one implementation of the present invention relating to a medical device connectable to a transseptal lead will be discussed. Preferably, a thin stylet or a lead with a small diameter, covered with an insulating layer, is used for penetration of septum. A small area on the distal part of the stylet is uncovered to form an electrode which can be used for measurements of cardiac signals such as impedance signals or IECG signals. Due to the conductivity differences between muscle or cardiac tissue and blood, a precise indication of the position of the electrode relative to the border between the cardiac tissue and blood, i.e. an indication whether the electrode has crossed the endocardium or not, can be obtained. The position of the stylet can be used as a reference for a placement of a transseptal stimulation lead. The IECG amplitude changes due to the distance to activated cardiac cells and to a smaller degree to differences in conductivity.

According to an embodiment of the present invention, the medical device 10 is connectable to one or more leads via an electrode configuration switch (not shown). In FIG. 1, the medical device is connected to one transseptal lead 20 arranged to be moved within a guiding catheter 21. A measuring unit 11 comprises a cardiac signal measuring device 12 configured to measure cardiac signals using a distal tip electrode 22 arranged on the lead 20 and a ring electrode 24 arranged on the guiding catheter 21.

Figure 2:
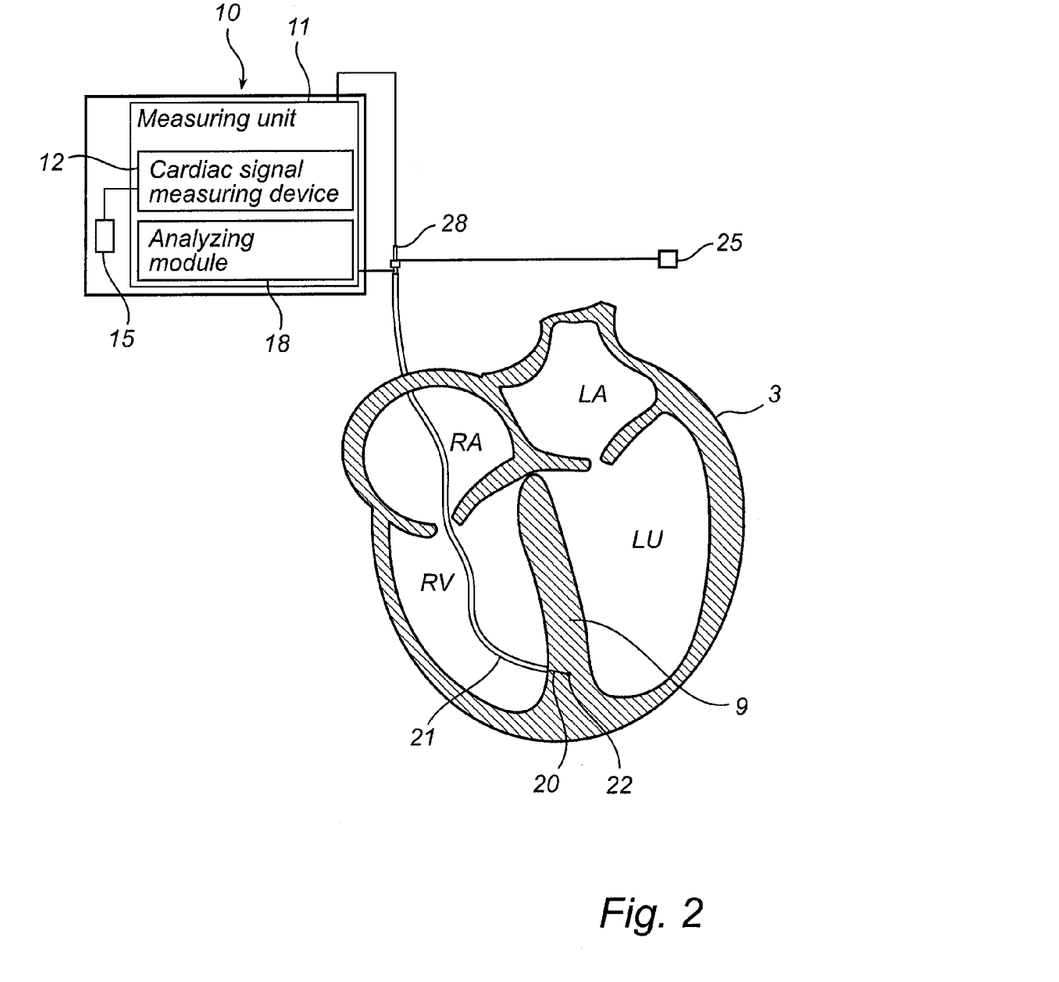
FIG. 2 is a simplified and schematic illustration of another embodiment of a medical device connected to a transseptal lead positioned within a heart.
Figure 3:
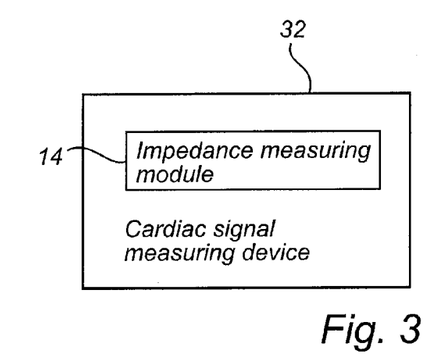
FIG. 3 is a schematic illustration of an embodiment of a cardiac signal measuring device according to the present invention.

According to one embodiment of the present invention shown in FIG. 3, the cardiac signal measuring device 32 comprises an impedance signal measuring module 14 having a current generating circuit configured to generate a current, for example, between the distal tip electrode 22 and the ring electrode 24 or, see FIG. 2, the tip electrode 22 and the plate electrode 25, which in embodiments of the present invention is placed outside the heart at a fixed position relative the heart. The resulting impedance is measured by a voltage measuring circuit of the impedance measuring module 14 between, for example, the same electrodes.

Figure 4:
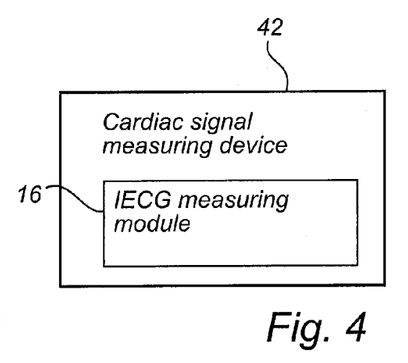
FIG. 4 is a schematic illustration of another embodiment of a cardiac signal measuring device according to the present invention.

According to another embodiment of the present invention shown in FIG. 4, the cardiac signal measuring device 42 comprises an IECG measuring module 16 configured to measure IECG signals using the distal tip electrode 22 and the electrode 24 or, see FIG. 2, the distal tip electrode 22 and the plate electrode 25.

Figure 5:
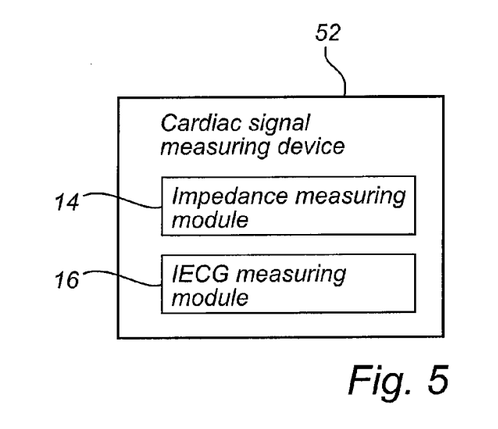
FIG. 5 is a schematic illustration of a further embodiment of a cardiac signal measuring device according to the present invention.

According to a further embodiment of the present invention shown in FIG. 5, the cardiac signal measuring device 52 comprises an impedance signal measuring module 14 and an IECG measuring module 16.

According to embodiments of the present invention, the cardiac signal measuring device 12 is configured to perform predetermined measurement sessions, which may occur at regular intervals or at receipt of an instruction, for example, from an analyzing module 18 of the measuring unit 11 or from an external device (not shown) communicating with the medical device. Preferably, the distal tip electrode 22 is moved forward into the tissue towards the tissue border at small steps between successive positions and the measurements are performed when the distal tip electrode 22 is held in a constant position relative the tissue border, i.e. has been stopped after it has been moved a small step from the previous position. Thus, a measurement session is performed at each stop. The measurement at the different sessions may have a length corresponding to a number of cardiac cycles and are synchronized with a transfer or advancement of the distal tip electrode 22 such that the measurements are performed when transfer of the distal tip electrode 22 is interrupted. For example, the distal tip electrode 22 may be advanced into the cardiac tissue, e.g. septum 9 of the heart 3, step-by-step at small increments of the advancement into tissue with short stops between each step and the measurements may be synchronized with the stops when the distal tip electrode 22 is not moving.

The analyzing module 18 is configured to acquire cardiac signals from the cardiac signal measuring device 12. Preferably, the cardiac signals are acquired at regular intervals and the acquired signals are measured during the predetermined measurement sessions. The analyzing module 18 is further configured to determine at least one cardiac signal value based on the cardiac signals for each measurement session. For example, the analyzing module 18 may be configured to determine impedance signal values based on the acquired impedance signals, e.g. the maximum amplitude over a cardiac cycle, the average maximum amplitude over a number of cardiac cycles, the peak-to peak value over a cardiac cycle, or the average peak-to-peak value over a number of cardiac cycles. The analyzing module 18 may alternatively be configured to determine IECG signal values based on acquired IECG signals, e.g. the maximum amplitude over a cardiac cycle, the average maximum amplitude over a number of cardiac cycles, the peak-to peak value over a cardiac cycle, the average peak-to-peak value over a number of cardiac cycles, the waveform morphology over a cardiac cycle, or the average morphology over a number of cardiac cycles. Furthermore, the analyzing module 18 may be configured to determine impedance signal values based on acquired impedance signals, such as the maximum amplitude over a cardiac cycle, the average maximum amplitude over a number of cardiac cycles, the peak-to peak value over a cardiac cycle, or the average peak-to-peak value over a number of cardiac cycles, the waveform morphology over a cardiac cycle, or the average morphology over a number of cardiac cycles and IECG signal values based on acquired IECG signals, such as the maximum amplitude over a cardiac cycle, the average maximum amplitude over a number of cardiac cycles, the peak-to peak value over a cardiac cycle, the average peak-to-peak value over a number of cardiac cycles, the waveform morphology over a cardiac cycle, or the average morphology over a number of cardiac cycles.

Furthermore, the analyzing module 18 is configured to analyze changes of the cardiac signal values between different measurement sessions to determine a position of the distal tip electrode 22 of the lead 20 relative a tissue border, wherein a maximum of the change of the cardiac signal values between two successive measurement sessions indicates that the distal tip electrode 22 has reached a desired position at the tissue border or very close to the tissue border. This will be discussed in more detail below with reference to FIGS. 6a-6c, and 7-9.

The aforementioned components may be implemented as part of a microcontroller (not shown), or as software/firmware instructions programmed into the device and executed on the microcontroller during certain modes of operation.

The measuring unit 11 may be coupled to a memory 15 by a suitable data/address bus (not shown), wherein, for example, programmable operating parameters used by the cardiac signal measuring device 12 are stored and modified. Such operating parameters define, for example, current amplitude, duration of measurement session, etc.

Moreover, the medical device 10 may additionally include a battery (not shown) that provides operating power to all of the circuits shown in FIGS. 1-5. Preferably, the medical device 10 employs lithium or similar battery technology.

Figure 6A:
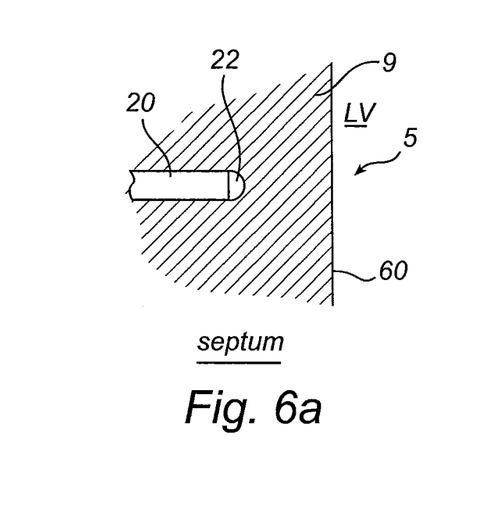
FIGS. 6a-6c are schematic diagrams illustrating a transseptal lead during different stages of a penetration course of septum.
Figure 6B:
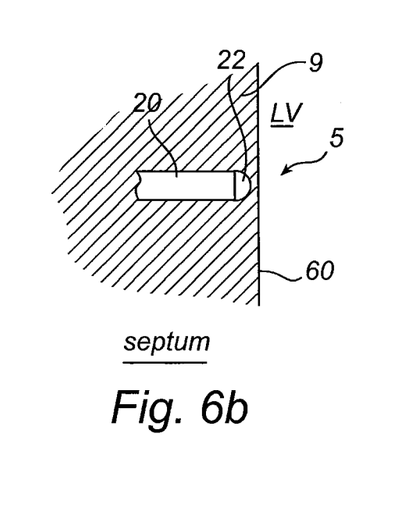
Figure 6C:
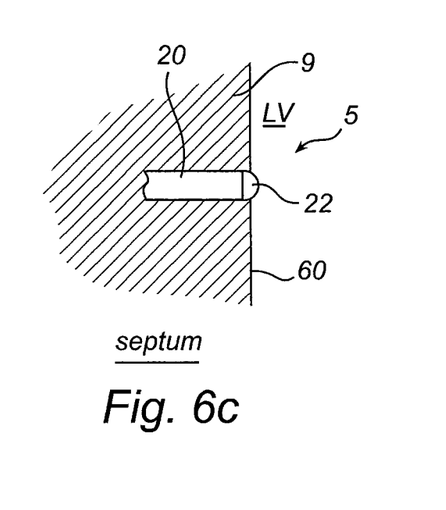
Figure 7:
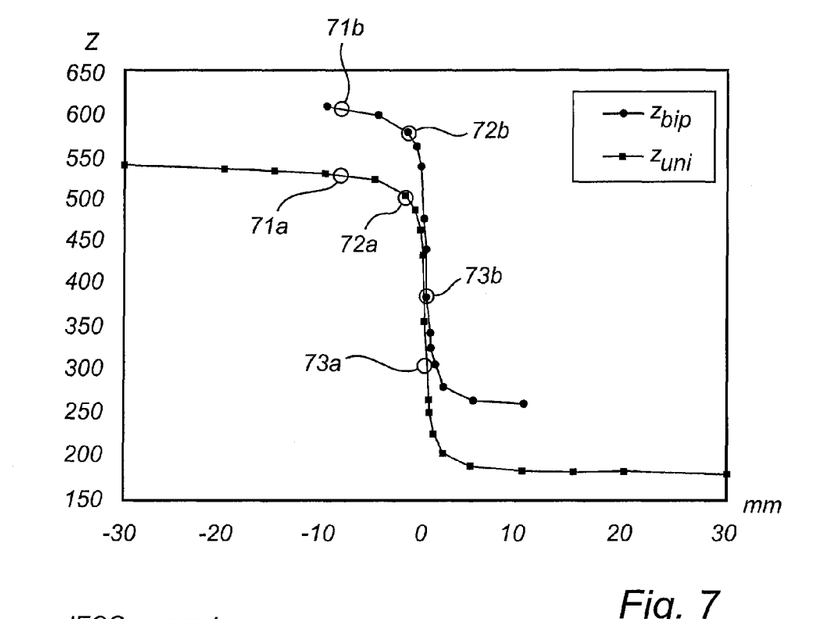
FIG. 7 is a diagram illustrating impedance signal values obtained at the different positions of the transseptal lead shown in FIGS. 6a-6c using the embodiment of the measuring device shown in FIG. 3.
Figure 8:
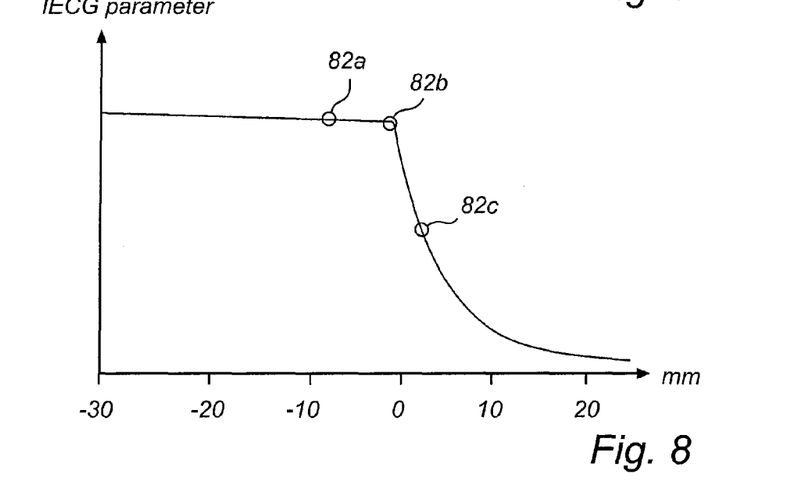
FIG. 8 is a diagram illustrating IECG signal values obtained at the different positions of the transseptal lead shown in FIGS. 6a-6c using the embodiment of the measuring device shown in FIG. 4.
Figure 9:
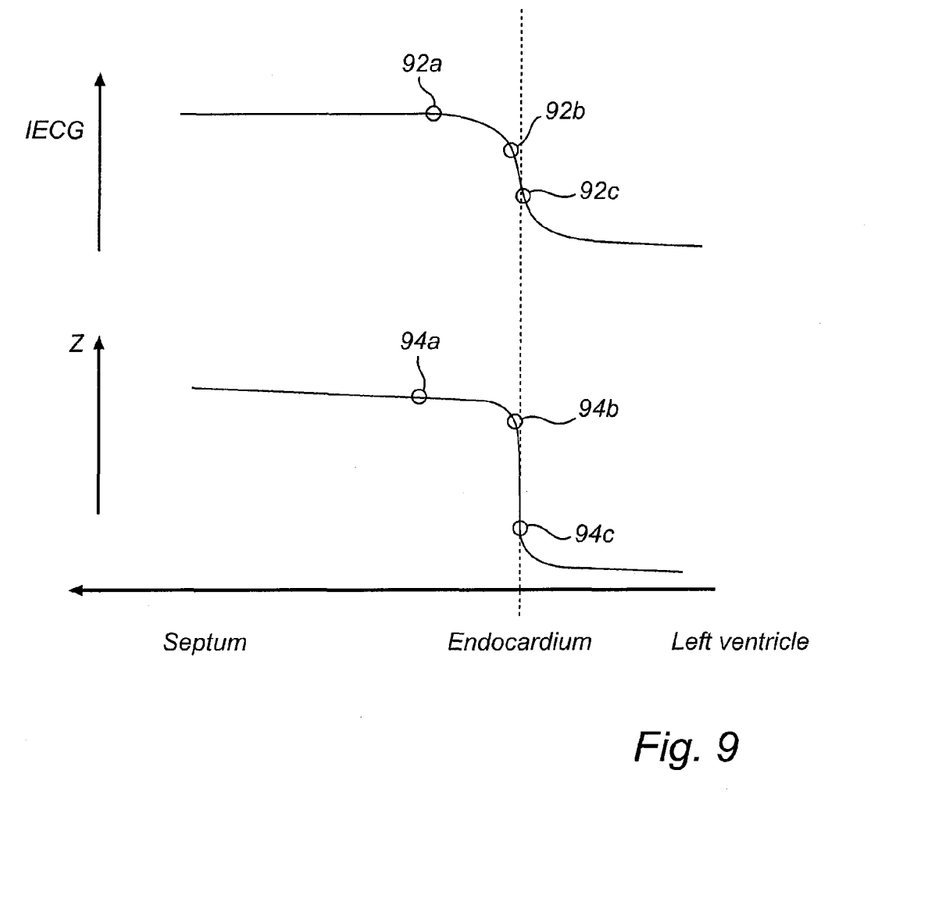
FIG. 9 is a diagram illustrating IECG signal values and impedance signal values obtained at the different positions of the transseptal lead shown in FIGS. 6a-6c using the embodiment of the measuring device shown in FIG. 5.

With reference now to FIGS. 6a-6c and 7-9, variations in the impedance and/or IECG signal values corresponding to different positions of the distal tip electrode 22 relative a tissue border are shown. FIGS. 6a-6c schematically illustrate different positions of the lead during an implantation procedure. FIG. 7 schematically shows impedance signal values obtained at different positions of the lead including the three positions shown in FIGS. 6a-6c (where $Z_{bip}$ indicates impedance values obtained using a bipolar electrode configuration and $Z_{uni}$ indicates values obtained using a unipolar configuration). FIG. 8 schematically shows IECG signal values obtained at different positions of the tip electrode 22 including the three positions shown in FIGS. 6a-6c. FIG. 9 schematically shows synchronous impedance signal values and IECG signal values obtained at different positions of the distal tip electrode 22 including the three positions shown in FIGS. 6a-6c.

Hence, the signal values obtained using the embodiment of the present invention shown in FIG. 3 are illustrated in FIG. 7, the signal values obtained using the embodiment of the present invention shown in FIG. 4 are illustrated in FIG. 8, and the signal values obtained using the embodiment of the present invention shown in FIG. 5 are illustrated in FIG. 9.

It should however be noted, that during use of the present invention, the lead is advanced in very small steps, for example 0.3-1 mm and the measurements are performed at each position. Hence, FIGS. 6a-6c are not drawn to scale and only intended for illustrational purposes.

In FIGS. 6a-6c, three different positions of the distal tip electrode 22 relative the tissue border 60, i.e. the border between the septum 9 and blood 5 of the left ventricle LV are shown. First, in FIG. 6a, the distal tip electrode 22 is positioned within septum 9. The signal values obtained in that position are indicated in FIGS. 7-9 as 71a, 71b, 82a, and 92a, 94a, respectively. In the second illustrated position, shown in FIG. 6b, the distal tip electrode 22 has been advanced further into septum 9 and is now positioned closer to the tissue border 60. The signal values obtained at this position are indicated as 72a, 72b, 82b, and 92b, 94b, respectively. As can be seen, in FIGS. 7-9, the signal values display small changes between these two positions and the change of the respective signal value expressed as a signal value derivative over traveled distance (for the lead) is small between these two positions.

Finally, in the third position, shown in FIG. 6c, the distal tip electrode 422 has reached the tissue border 60 or endocardium and is positioned at the tissue border 60 or endocardium. The signal values obtained at this position are indicated as 73a, 73b, 83c, and 92c, 94c, respectively. As can be seen, the signal values have changed drastically between this position and the preceding position shown in FIG. 6b. By observing the change of the signal values from position to position, i.e. the derivative of the signal waveform over length, the position of the distal tip electrode 22 relative the tissue border 60 can be determined very accurately. When the change of the signal values from one position to the next reaches a maximum, i.e. at a maximum derivative of the signal value waveform, the electrode 22 is at the tissue border 60.

Although certain embodiments and examples have been described herein, it will be understood by those skilled in the art that many aspects of the devices and methods shown and described in the present disclosure may be differently combined and/or modified to form still further embodiments. Alternative embodiments and/or uses of the devices and methods described above and obvious modifications and equivalents thereof are intended to be within the scope of the present disclosure. Thus, it is intended that the scope of the present invention should not be limited by the particular embodiments described above, but should be determined by a fair reading of the claims that follow.

The invention claimed is:

1. A medical device for determining a desired position at a tissue border of a medical lead having a distal tip being arranged to enable penetration of cardiac tissue, said lead being connectable to a measuring unit of said medical device at a proximal end, wherein said measuring unit comprises:
   a cardiac signal measuring device configured to measure cardiac signals sensitive to inherent differences between cardiac tissue and blood using at least one electrode arranged at said distal tip of said medical lead and at least a second electrode arranged at a distance from said distal tip electrode and being connectable to said measuring unit; and
   an analyzing module configured to communicate with said cardiac signal measuring device, said analyzing module being further configured to:
      acquire cardiac signals from said cardiac signal measuring device measured at predetermined measurement sessions;
      determine at least one cardiac signal value based on the cardiac signals for each measurement session; and
      analyze changes of the cardiac signal values between different measurement sessions to determine a position of said distal tip electrode of said lead relative a tissue border, wherein a maximum of the change of the cardiac signal values between two successive measurement sessions indicates that the distal tip electrode has reached the desired position at said tissue border;
   wherein said cardiac signal measuring device comprises an intracardiac electrogram, IECG, measuring module configured to measure IECG signals and an impedance measuring module configured to measure impedance signals, and wherein said analyzing module is configured to:
      acquire IECG signals from said IECG measuring module and impedance signals from said impedance measuring module measured at predetermined measurement sessions;
      determine at least one IECG signal value based on the IECG signals and at least one impedance signal value based on the impedance signals for each measurement session; and
      analyze changes of the IECG signal values and the impedance signal values between different measurement sessions to determine a position of said distal tip electrode relative a tissue border, wherein a maximum of the change of the IECG signal values and impedance signal values between two successive measurement sessions indicates that the distal tip electrode has reached the desired position at said tissue border; and
   wherein said measuring unit is configured to synchronize impedance signal measurements and IECG signal measurements in time during the measurement sessions, and wherein said analyzing module is configured to:
      acquire impedance signals and IECG signals from said impedance signal measuring module and IECG measuring module measured at synchronized and predetermined measurement sessions;
      determine the synchronized impedance signal values and/or IECG signal values for each measurement session; and
      analyze synchronous changes of the impedance signal values and the IECG signal values to determine a position of said distal tip electrode relative to a tissue border, wherein a synchronous maximum of a change of the impedance signal values and the IECG signal values between two successive measurement sessions indicates that the distal tip electrode has reached the desired position at said tissue border.

2. The device according to claim 1, wherein said medical lead is a transseptal lead.

3. The device according to claim 1, wherein said at least one second electrode is a ring electrode arranged on a guiding catheter, said guiding catheter being arranged to guide said lead during penetration of tissue.

4. The device according to claim 1, wherein said at least one second electrode is arranged to be in a position outside the heart and is arranged to be connected to said measuring unit.

5. A medical device for determining a desired position at a tissue border of a medical lead having a distal tip being arranged to enable penetration of cardiac tissue, said lead being connectable to a measuring unit of said medical device at a proximal end, wherein said measuring unit comprises:
   a cardiac signal measuring device configured to measure cardiac signals sensitive to inherent differences between cardiac tissue and blood using at least one electrode arranged at said distal tip of said medical lead and at least a second electrode arranged at a distance from said distal tip electrode and being connectable to said measuring unit; and
   an analyzing module configured to communicate with said cardiac signal measuring device, said analyzing module being further configured to:
      acquire cardiac signals from said cardiac signal measuring device measured at predetermined measurement sessions;
      determine at least one cardiac signal value based on the cardiac signals for each measurement session; and
      analyze changes of the cardiac signal values between different measurement sessions to determine a position of said distal tip electrode of said lead relative a tissue border, wherein a maximum of the change of the cardiac signal values between two successive measurement sessions indicates that the distal tip electrode has reached the desired position at said tissue border;
   wherein said cardiac signal measuring device comprises an impedance measuring module configured to measure impedance signals, and wherein said analyzing module is configured to:
      acquire impedance signals from said impedance signal measuring module measured at predetermined measurement sessions;
      determine at least one impedance signal value based on the impedance signals for each measurement session; and
      analyze changes of the impedance signal values between different measurement sessions to determine a position of said distal tip electrode relative a tissue border, wherein a maximum of the change of the impedance signal values between two successive measurement sessions indicates that the distal tip electrode has reached the desired position at said tissue border; and
wherein said cardiac signal measuring device comprises an intracardiac electrogram, IECG, measuring module configured to measure IECG signals, and wherein said analyzing module is configured to:
determine a QRS-waveform for each cardiac cycle using said IECG signals;
synchronize the impedance signal values with said QRS-waveforms; and
analyze changes between different measurements of the impedance signal values coinciding with a certain point of the QRS-waveform to determine a position of said distal tip electrode relative a tissue border, wherein a maximum of the change of the impedance signal values between two successive measurement sessions indicates that the distal tip electrode has reached the desired position at said tissue border.

6. A method for determining a desired position at a tissue border of a medical lead having a distal tip being arranged to enable penetration of cardiac tissue, wherein said method comprises:
measuring cardiac signals sensitive to inherent differences between cardiac tissue and blood using at least one electrode arranged at said distal tip of said medical lead and at least a second electrode arranged at a distance from said distal tip electrode;
acquiring cardiac signals measured at predetermined measurement sessions;
determining at least one cardiac signal value based on the cardiac signals for each measurement session;
analyzing changes of the cardiac signal values between different measurement sessions to determine a position of said distal tip electrode relative a tissue border, wherein a maximum of the change of the cardiac signal values between two successive measurement sessions indicates that the distal tip electrode has reached the desired position at said tissue border;
acquiring IECG signals and impedance signals measured at predetermined measurement sessions;
determining at least one IECG signal value based on the IECG signals and at least one impedance signal value for each measurement session;
analyzing changes of the IECG signal values and the impedance signal values between different measurement sessions to determine a position of said distal tip electrode relative a tissue border, wherein a maximum of the change of the IECG signal values and impedance signal values between two successive measurement sessions indicates that the distal tip electrode has reached the desired position at said tissue border;
synchronizing impedance signal measurements and IECG signal measurements in time during the measurement sessions;
acquiring impedance signals and IECG signals measured at synchronized and predetermined measurement sessions;
determining the synchronized impedance signal values and/or IECG signal values for each measurement session; and
analyzing synchronous changes of the impedance signal values and the IECG signal values to determine a position of said distal tip electrode relative to a tissue border, wherein a synchronous maximum of a change of the impedance signal values and the IECG signal values between two successive measurement sessions indicates that the distal tip electrode has reached the desired position at said tissue border.

7. A method for determining a desired position at a tissue border of a medical lead having a distal tip being arranged to enable penetration of cardiac tissue, wherein said method comprises:
measuring cardiac signals sensitive to inherent differences between cardiac tissue and blood using at least one electrode arranged at said distal tip of said medical lead and at least a second electrode arranged at a distance from said distal tip electrode;
acquiring cardiac signals measured at predetermined measurement sessions;
determining at least one cardiac signal value based on the cardiac signals for each measurement session;
analyzing changes of the cardiac signal values between different measurement sessions to determine a position of said distal tip electrode relative a tissue border, wherein a maximum of the change of the cardiac signal values between two successive measurement sessions indicates that the distal tip electrode has reached the desired position at said tissue border;
acquiring impedance signals measured at predetermined measurement sessions;
determining at least one impedance signal value based on the impedance signals for each measurement session;
analyzing changes of the impedance signal values between different measurement sessions to determine a position of said distal tip electrode relative a tissue border, wherein a maximum of the change of the impedance signal values between two successive measurement sessions indicates that the distal tip electrode has reached the desired position at said tissue border;
determining a QRS-waveform for each cardiac cycle using measured IECG signals;
synchronizing the impedance signal values with said QRS-waveforms; and
analyzing changes between different measurements of the impedance signal values coinciding with a certain point of the QRS-waveform to determine a position of said distal tip electrode relative a tissue border, wherein a maximum of the change of the impedance signal values between two successive measurement sessions indicates that the distal tip electrode has reached the desired position at said tissue border.

* * * * *